(12) United States Patent  (10) Patent No.: US 6,369,275 B1
Davies et al.  (45) Date of Patent: Apr. 9, 2002

(54) PROCESS FOR MAKING DIARYL PYRIDINES USEFUL AS COX-2 INHIBITORS

(75) Inventors: Ian W. Davies, Princeton; Michel Journet, Somerset; Linda Gerena, Piscataway; Robert D. Larsen, Bridgewater; Philip J. Pye, Guttenberg; Kai Rossen, Westfield, all of NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/715,736

(22) Filed: Nov. 17, 2000

Related U.S. Application Data

(62) Division of application No. 09/509,230, filed as application No. PCT/US98/19788 on Sep. 22, 1988
(60) Provisional application No. 60/060,680, filed on Sep. 25, 1997.

(51) Int. Cl.[7] .......................... C07C 22/04; C07C 22/08; C07C 321/24
(52) U.S. Cl. .......................... 568/56; 570/235; 570/182
(58) Field of Search ................ 570/182, 235; 568/194, 56

(56) References Cited

U.S. PATENT DOCUMENTS

| 3,277,103 A | 10/1966 | Trofimenko |
| 5,480,568 A | 1/1996 | Pawloski et al. |
| 5,593,994 A | 1/1997 | Batt et al. |
| 5,686,470 A | 11/1997 | Weier |

FOREIGN PATENT DOCUMENTS

| DE | 36 34 259 | 10/1986 |
| EP | 0 017438 | 10/1980 |
| EP | 0 075727 | 4/1983 |
| EP | 0 548559 | 6/1993 |
| WO | WO 96 10012 | 4/1996 |
| WO | WO 96 21667 | 7/1996 |
| WO | WO 96 16934 | 11/1997 |
| WO | WO 96 24584 | 11/1997 |

OTHER PUBLICATIONS

Caplus English Abstract 132:50011 Nell Peter G. New J. Chem. 1999 vol. 23 Issue 10 pp. 973–975 Nov. 1999.*
Gronowitz, S. et al.; Chem. Abs., vol. 91, No. 23, Abs. No. 193249, 1979.
Skoetsch, C., et al.; Chem. Abs., vol. 92, No. 21, Abs. No. 180583, 1980.
Hanke, R., et al.; Chem. Abs., vol. 96, No. 25, Abs. No. 217817, 1982.
Tietze, L. F., et al.; Chem. Abs., vol. 99, No. 19, Abs. No. 158202, 1983.
Kania, L., et al.; Chem. Abs., vol. 101, No. 13, Abs. No. 109885, 1984.
Fabian W.; Chem. Abs., vol. 103, No. 13, Abs. No. 104142, 1985.
Tietze, L. F., et al.; Chem. Abs., vol. 110, No. 9, Abs. No. 74786, 1989.
Arnold, Z., et al.; Chem. Abs., vol. 115, No. 7, Abs. No. 70882, 1991.
Linstroem, S. Chem. Abs. vol. 123, No. 17, Abs. No. 228067, 1995.
Kajigaeshi, S. et al.; Chem. Abs., vol. 115, No. 13, Abs. No. 135894, 1991.
Thummel, R. et al.; J. Org. Chem. vol. 42, No. 16, pp. 2742–2747, 1977.
Adachi, J. et al.; Chem. Pharm. Bull., vol. 24, No. 1, pp. 85–91, 1976.
Breitmaier, E., et al; Chem. Abs., vol. 74, No. 17, Abs. No. 87279, 1971.

* cited by examiner

*Primary Examiner*—Alan L. Rotman
*Assistant Examiner*—Rita Desai
(74) *Attorney, Agent, or Firm*—Raynard Yuro; Richard C. Billups; David L. Rose

(57) ABSTRACT

The invention encompasses a process for making compounds of Formula I useful in the treatment of cyclooxygenase-2 mediated diseases.

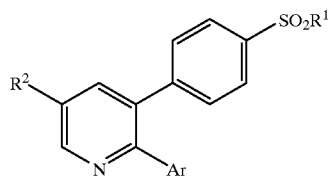

I

6 Claims, No Drawings

PROCESS FOR MAKING DIARYL PYRIDINES USEFUL AS COX-2 INHIBITORS

This application is a divisional of U.S. application Ser. No., 09/509,230 which was the U.S. National Phase of PCT Application No. US98/19788 filed Sep. 22, 1988, which claimed the benefit of U.S. application Ser. No. 60/060,680 filed on Sep. 25, 1997 priority of which is claimed hereunder.

BACKGROUND OF THE INVENTION

This invention concerns a process for making certain anti-inflammatory compounds. In particular, the application concerns a process for making compounds of formula I as disclosed hereinunder, which compounds are potent cyclooxygenase-2 inhibitors.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

WO 96/24585 published Aug. 15, 1996 and WO 96/10012, published Apr. 4, 1996 disclose methods of making 2-aryl-3-aryl-pyridines. In the invention as disclosed hereinunder, 2-aryl-3-aryl-pyridines are prepared in a simple to conduct, 2 step conversion of a Weinreb amide to the penultimate ketosulfone from readily available starting materials. It is, therefore, surprisingly convenient and more efficient than the previously described procedure, in which the 2-aryl-3-aryl pyridine was constructed by serial stepwise addition of the aryl groups to the central pyridine ring. Moreover, the process of the instant invention is also surprisingly superior in that expensive palladium reagents are not required nor is the cumbersome protection/deprotection sequense of the prior art process.

SUMMARY OF THE INVENTION

The invention encompasses a process for making cyclooxygenase-2 intermediates such as the compound of structural formula 5.

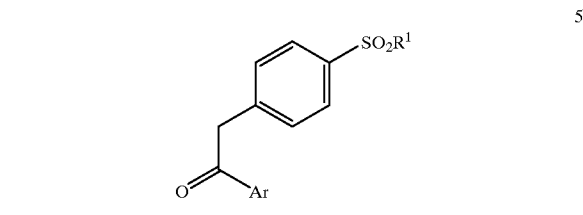

5

Compound 5 is useful in making potent cyclooxygenase-2 inhibitors of structural formula I, which are useful in the treatment of inflammation and other cyclooxygenase-2 mediated diseases

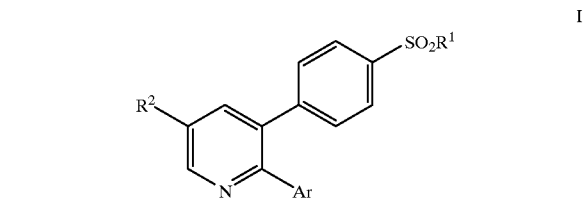

I wherein:
  $R^1$ is selected from the group consisting of
    (a) $CH_3$,
    (b) $NH_2$,
    (c) $NHC(O)CF_3$,
    (d) $NHCH_3$;
  Ar is a mono-, di-, or trisubstituted phenyl or pyridinyl (or the N-oxide thereof), wherein the substituents are chosen from the group consisting of
    (a) hydrogen,
    (b) halo,
    (c) $C_{1-4}$alkoxy,
    (d) $C_{1-4}$alkylthio,
    (e) CN,
    (f) $C_{1-4}$alkyl,
    (g) $C_{1-4}$fluoroalkyl, and
  $R^2$ is chosen from the group consisting of
    (a) F, Cl, Br, I
    (b) CN,
    (c) azide.

DETAILED DESCRIPTION OF THE INVENTION

In a first aspect, the invention encompasses a process for making a compound of Formula 5, which is a COX-2 intermediate,

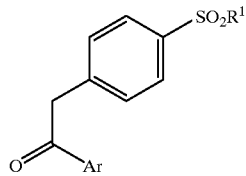

5 the process comprising:

reacting a compound of formula 13

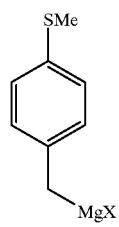

13 wherein X is a halogen belonging to the group consisting of chlorine, bromine and fluorine, with a compound of formula 9

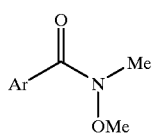

9 wherein Ar is a mono-, di-, or trisubstituted phenyl or pyridinyl (or the N-oxide thereof), wherein the substituents are chosen from the group consisting of
(a) hydrogen,
(b) halo,
(c) $C_{1-4}$alkoxy,
(d) $C_{1-4}$alkylthio,
(e) CN,
(f) $C_{1-4}$alkyl,
(g) $C_{1-4}$fluoroalkyl, to yield a compound of formula 15

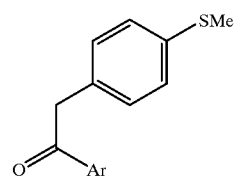

15 wherein Ar is described above, and oxidizing the compound of formula 15 using an oxidizing agent, and optionally a catalyst and an acid to yield a compound of formula 5.

In a second aspect, the invention encompasses a process for making a compound of formula 13

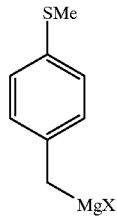

13 wherein X is a halogen belonging to the group consisting of chlorine, bromine and fluorine, comprising reacting a compound of formula 12

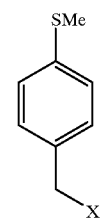

12 with magnesium in the presence of a solvent/co-solvent mixture to yield a compound of formula 13.

In a third aspect, the invention encompasses a process for making a compound of formula I

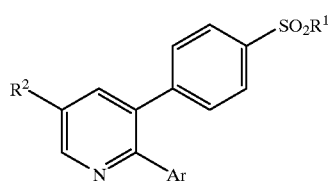

I wherein:

$R^1$ is selected from the group consisting of
(a) $CH_3$,
(b) $NH_2$,
(c) $NHC(O)CF_3$,
(d) $NHCH_3$;

Ar is a mono-, di-, or trisubstituted phenyl or pyridinyl (or the N-oxide thereof), wherein the substituents are chosen from the group consisting of
(a) hydrogen,
(b) halo,
(c) $C_{1-4}$alkoxy,
(d) $C_{1-4}$alkylthio,
(e) CN,
(f) $C_{1-4}$alkyl,
(g) $C_{1-4}$fluoroalkyl, and $R^2$ is chosen from the group consisting of
(a) F, Cl, Br, I
(b) CN,
(c) azide;

comprising reacting a compound of formula 12

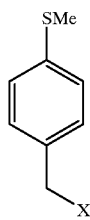

wherein X is a halogen belonging to the group consisting of iodine, chlorine, bromine and fluorine,
with magnesium in the presence of a solvent/co-solvent mixture to yield a compound of formula 13

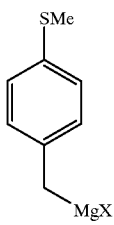

reacting the compound of formula 13 with a compound of formula 9

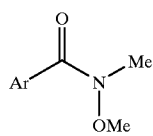

wherein Ar is described above,
to yield a compound of formula 15

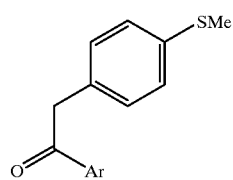

wherein Ar is described above,
and oxidizing the compound of formula 15 using an oxidizing agent and optionally a catalyst under acid conditions to yield a compound of formula 5

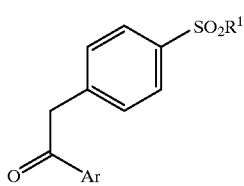

wherein R1 is described above, condensing a compound of formula A1 or A2

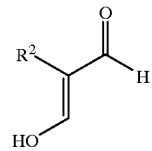

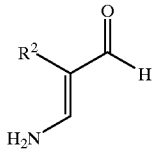

under acidic conditions, optionally in the presence of a non-reactive solvent and in the presence of an ammonium reagent, with compound 5 to yield a compound of Formula I.

In a fourth aspect of the invention, the process encompasses a method for making a compound of formula II:

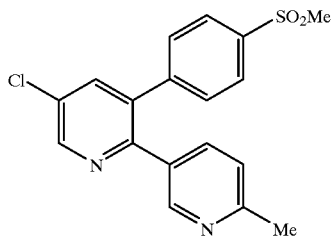

comprising reacting a compound of formula 12

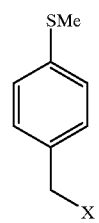

wherein X is a halogen belonging to the group consisting of iodide, chloride, bromide and fluoride;
with magnesium in the presence of a solvent/co-solvent mixture to yield a compound of formula 13

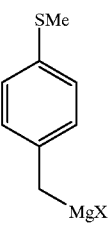

reacting the compound of formula 13 with a compound of formula 9a

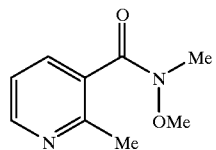

to yield a compound of formula 15a

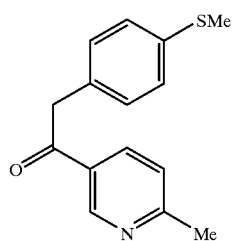

and oxidizing the compound of formula 15a using an oxidizing agent and optionally a catalyst under acid conditions to yield a compound of formula

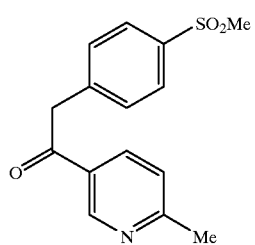

condensing a compound of formula A1 or A2

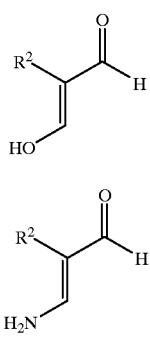

wherein $R^2$ is F, Cl, Br, I, CN, or azide;
under acidic conditions, and optionally in the presence of a non-reactive solvent and in the presence of an ammonium reagent, with compound 5a
to yield a compound of Formula II.

A further aspect of this invention is realized when A1 is employed wherein the acidic condition consists of the addition of acetic or propionic acid, the non-reactive solvent is tetrahydrofuran, dioxane, $C_{1-6}$alkanol, chlorobenzene, dichlorobenze, xylene or toluene and the ammonium reagent is ammonia, ammonium acetate or ammonium propionate.

A further aspect of this invention is realized when A2 is employed wherein the acidic condition consists of the addition of acetic acid, methanesulfonic acid or propionic acid or a mixture thereof, preferably a mixture of propionic acid and methanesulfonic acid, the non-reactive solvent is tetrahydrofuran, dioxane, $C_{1-6}$alkanol, chlorobenzene, dichlorobenze, xylene or toluene and the ammonium reagent is ammonia, ammonium acetate, ammonium hydroxide and ammonium propionate, preferably ammonium hydroxide.

For purposes of this specification, the reactions, unless otherwise specified, are generally carried out in a solvent such as benzene, chlorobenzene, dichlorobenze, toluene and xylene; etheral solvents such as diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, 2-ethoxytetrahydrofuran and tetrahydrofuran (THF); ester solvents including ethyl and isopropyl acetate; halo carbon solvents including mono or dihalo $C_{1-4}$ alkyl such as dichloromethane; $C_{6-10}$ linear, branched or cyclic hydrocarbon solvents including hexane; and nitrogen containing solvents including N,N-dimethylacetamide, N,N-dimethylformamide (DMF), N-ethylpyrrolidinone, N-methylpyrrolidinone, and acetonitrile. Preferable solvents are alcohol, dichloromethane, THF and DMF.

For purposes of this specification X is a halogen belonging to the group consisting of iodide, chloride, bromide or fluoride, preferably chloride and compound 12 is commercially available.

Regarding the first aspect of the invention, the oxidizing agent belongs to the group consisting of hydrogen peroxide, oxone, hydrogen peroxide/acetic acid and the like, preferably oxone or hydrogen peroxide and the catalyst is $Na_2WO_4$. The acid shall include acetic, propionic or another carboxylic acid, hydrochloric acid or sulfuric acid and the like. The pH is maintained at about 2 to about 5, preferably about 2–4. The reaction is preferably conducted employing an acid such as sulfuric acid.

The molar ratio of 13 to 9 can typically be varied from about 1:1 to about 2:1; preferably about 1:5 to about 1. Excess compound 13 relative to compound 9 is typically used. The molar ratio of compound 15 to oxidizing agent can typically be varied from about 1:1 to about 1:10. The molar ratio of the catalyst to compound 15 can typically be varied from about 1:1 to about 1:1000, preferably about 1:100. The reaction may conveniently be conducted at a temperature range of about 0 to about 100° C.; preferably about 50 to about 60° C. and is allowed to proceed until substantially complete in from 1 to 24 hours.

For purposes of this specification, in the second aspect of the invention the solvent/co-solvent mixture shall include solvent mixtures such as toluene/tetrahydrofuran, tetrahydrofuran/diethylether, toluene/diethylether, tetrahydrofuran/methyl-t-butylether, toluene/methyl-t-butylether, toluene/dioxane, tetrahydrofuran/dioxane and the like, preferably toluene/tetrahydrofuran.

The molar ratio of compound 12 to solvent/co-solvent mixture can typically be varied from about 1:20 to about 1:1, preferably about 1:3 to about 1:1. The molar ratio of solvent to co-solvent can typically be varied from about 0.5:4 to about 1:1, preferably about 1:2 to about 1:1. The molar ratio of compound 12 to magnesium can typically be varied from about 1:2 to about 1:1. Generally, compound 12 is mixed with the required amount of co-solvent and added to the solvent containing magnesium and the reaction is conveniently conducted at a temperature range of about 0 to about 40° C.; preferably about 10 to about 35° C. The reaction is allowed to proceed until substantially complete in from 1 to 5 hours; typically 1 to 2 hours.

Regarding the third aspect of the invention, as will be appreciated by those of skill in the art, in the general case the reagents themselves provide the acidic condition. Therfore, the use of a non-reagent acid is not necessary. However, the addition of an acid, such as acetic or propionic or another carboxylic acid or a mixture of acids such as propionic acid and methanesulfonic acid are within the scope of the invention.

For purposes of this specification non-reactive solvent includes tetrahydrofuran, dioxane, $C_{1-6}$alkanol, chlorobenzene, dichlorobenze, xylene and toluene.

For purposes of this specification, the ammonium reagent is intended to include ammonia, ammonim salts such as ammonium acetate and ammonium propionate and aqueous ammonia such as ammonium hydroxide. Moreover a mixture ammonia reagent species is included in the term ammonia reagent.

The molar ratio of compound A1 or A2 to 5 can typically be varied from about 3:1 to about 1:2; preferably about 1:1 to about 1.5. Excess compound Al is typically used. The molar ratio of compound A1 or A2 to ammonium reagent can typically be varied from about 1:1 to about 1:10. The reaction step may conveniently be conducted at a temperature range of about 40 to about 180° C.; preferably about 80 to about 140° C. and is allowed to proceed until substantially complete in from about 2 to about 18 hours; typically about 6 to about 12 hours.

With regard to the third aspect of the invention, $R^2$ is preferably halogen, most preferably F, Br, or Cl, most preferably Cl.

With regard to all aspects of the invention a preferred sub-genus of formula I is that wherein Ar is a mono-, or disubstituted pyridinyl. Within this sub-genus, the 3-pyridinyl isomers are particularly preferred.

Again with regard to all aspects of the invention another preferred sub-genus of formula I is that wherein $R^1$ is $CH_3$ or $NH_2$. Generally, $CH_3$ is preferred for COX-2 specificity and $NH_2$ is preferred for potency.

Again with regard to all aspects of the invention another preferred sub-genus of formula I is that wherein the Ar is unsubstituted or substituted with $CH_3$.

In a fifth aspect of the invention the compounds of formula A2 are described:

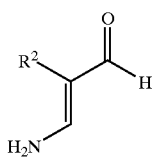

A2 wherein $R^2$ is:
(a) halogen
(b) CN,
(c) azide
(d) $C_{2-6}$ alkyl optionally substituted with 1 to 3 groups of $C_{1-6}$ alkyl, hydroxy, halogen, carbonyl, $CO_2$, $NO_2$, $OC_{1-6}$ alkyl; $SC_{1-6}$ alkyl, $N(C_{1-6}$ alkyl$)_2$
(e) $C_{5-10}$ aryl or heteroaryl optionally substituted with 1 to 3 groups of $C_{1-6}$ alkyl, hydroxy, halogen, carbonyl, $CO_2$, NO2, $OC_{1-6}$ alkyl; $SC_{1-6}$ alkyl, $N(C_{1-6}$ alkyl$)_2$.

A preferred compound is realized when $R^2$ is halogen, alkyl, phenyl or substituted phenyl. Most preferably compounds are realized when $R^2$ is fluorine, bromine, iodine, chlorine, ethyl, isopropyl, phenyl, trifluorophenyl As used herein, "alkyl" is intended to include branched, cyclic and straight-chain saturated aliphatic hydrocarbon groups having the specified number of carbon atoms. Examples of cycloalkyl groups include cyclopropyl, cyclobutyl, cyclopentyl, cyclohexyl and the like.

As used herein, "aryl" is intended to include aryls and heteroaryls, both substituted and unsubstituted, which are defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl as well as aromatic rings e.g., phenyl, substituted phenyl and like groups as well as rings which are fused, e.g., naphthyl and the like. Substitution can be 1 to 3 groups of $C_{1-6}$ alkyl, hydroxy, halogen, carbonyl, $CO_2$, NO2, $OC_{1-6}$ alkyl; $SC_{1-6}$ alkyl, $N(C_{1-6}$ alkyl$)_2$ and the like.

As used herein, "halogen" is intended to include chlorine, fluorine, bromine and iodine.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (ie Alzheimer's dementia).

By virtue of its high cyclooxygenase-2 (COX-2) activity and/or its selectivity for cyclooxygenase-2 over cyclooxygenase-1 (COX-1) as defined above, compounds of formula I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptable to NSAID induced asthma.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The IC50 values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 IC50 of 1 nM to 1 mM. By way of comparison, Ibuprofen has an IC50 for COX-2 of 1 mM, and Indomethacin has an IC50 for COX-2 of approximately 100 nM.

For the treatment of any of these cyclooxygenase mediated diseases, compounds of formula I may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The invention will now be illustrated by the following non-limiting examples in which, unless stated otherwise:

(i) all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) or High Pressure Liquid Chromatography (HPLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

The following abbreviations have the indicated meanings:
Alkyl Group Abbreviations Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl

EXAMPLE 1

5-Chloro-3(methylsulfonyl)phenyl-2-(3-pyridyl)-pyridine; Compound 1

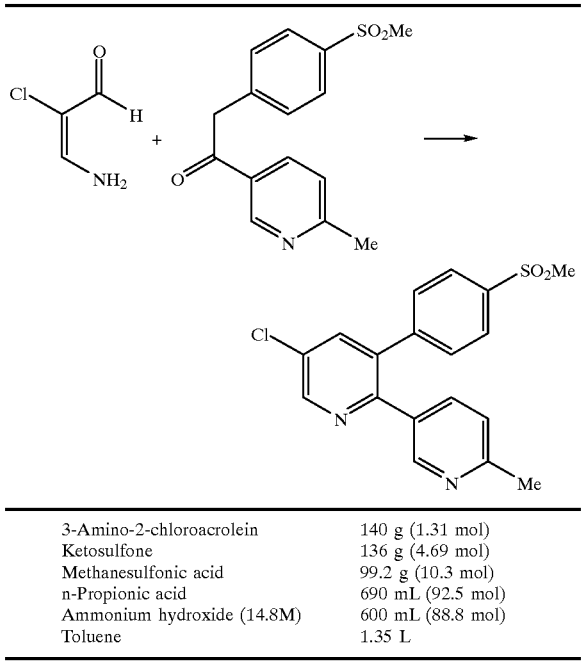

| 3-Amino-2-chloroacrolein | 140 g (1.31 mol) |
| Ketosulfone | 136 g (4.69 mol) |
| Methanesulfonic acid | 99.2 g (10.3 mol) |
| n-Propionic acid | 690 mL (92.5 mol) |
| Ammonium hydroxide (14.8M) | 600 mL (88.8 mol) |
| Toluene | 1.35 L |

A mixture of n-propionic acid (400 mL), 3-amino-2-chloroacrolein (140 g, 1.31 mol), ketosulfone (136 g, 0.469 mol), toluene (1.35 L), propionic acid (690 mL, 92.5 mol), methanesulfonic acid (67 mL, 10.3 mol) was heated to reflux (114° C.) for 12 hours with the azeotropic removal of water. The reaction solution was cooled to ambient temperature and diluted with isopropyl acetate (1 L). Water (1 L) was added and the aqueous phase was neutralized with concentrated ammonium hydroxide solution (600 mL). The organic layer was washed with a 1:1 mixture of brine/water (2×1 L) and water (1 L). The combined aqueous layers were extracted with isopropyl acetate (900 mL). The combined organic layers were treated with Darco G-60 then concentrated. Recrytallization from isopropylacetate/hexanes gave a colorless solid (123.1 g, 65%) mp 135° C. (DSC).

EXAMPLE 1A

5-Chloro-3(methylsulfonyl)phenyl-2-(3-pyridyl)-pyridine; Compound 1

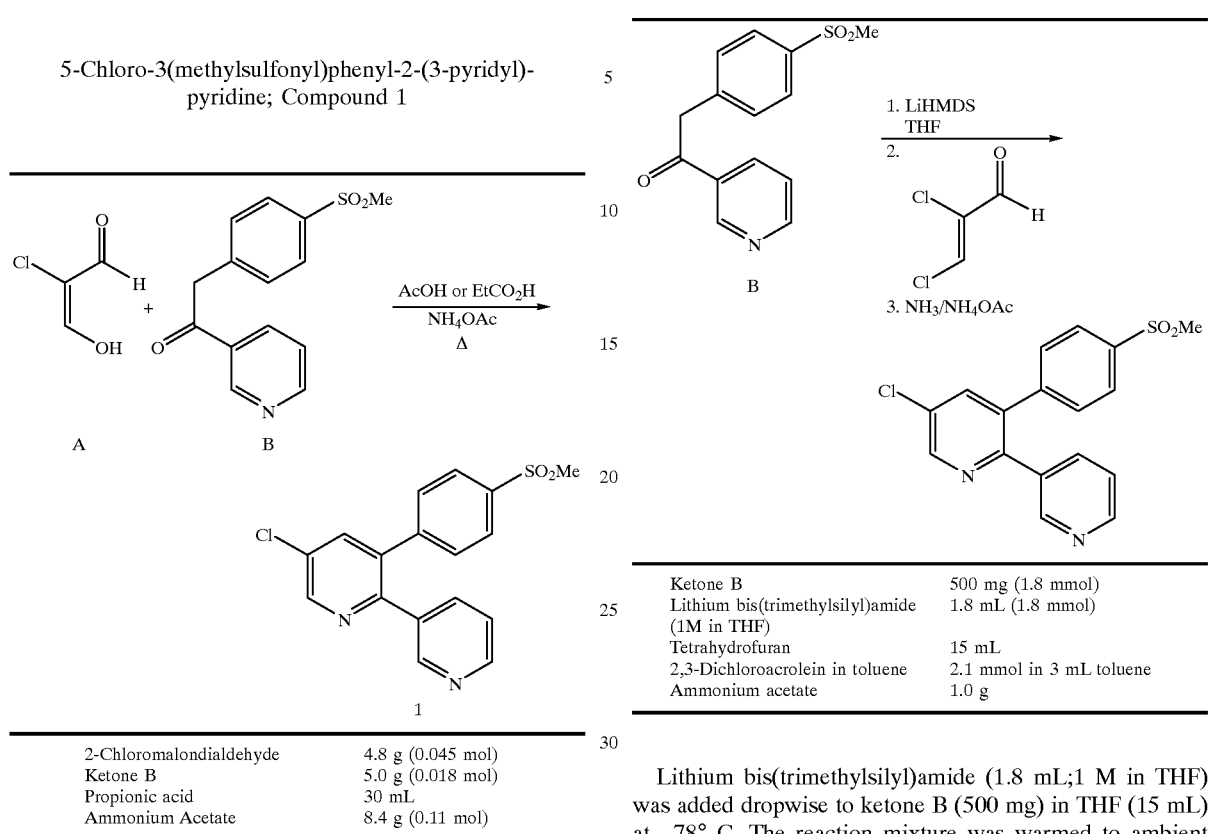

| | |
|---|---|
| 2-Chloromalondialdehyde | 4.8 g (0.045 mol) |
| Ketone B | 5.0 g (0.018 mol) |
| Propionic acid | 30 mL |
| Ammonium Acetate | 8.4 g (0.11 mol) |

A mixture of ketone B (5.0 g), 2-chloromalondialdehyde (4.8 g) and ammonium acetate were heated to 130° C. The acetic acid produced was removed by distillation and heating continued at 136° C. for 15 hours. The reaction mixture was basified with sodium carbonate, water was added and the product was extracted into dichloromethane (2×150 mL). The organic layers were carbon treated (Dowex), dried (MgSO$_4$) and the solvent removed to afford 1 as an off white solid (3.4 g, 55% yield).

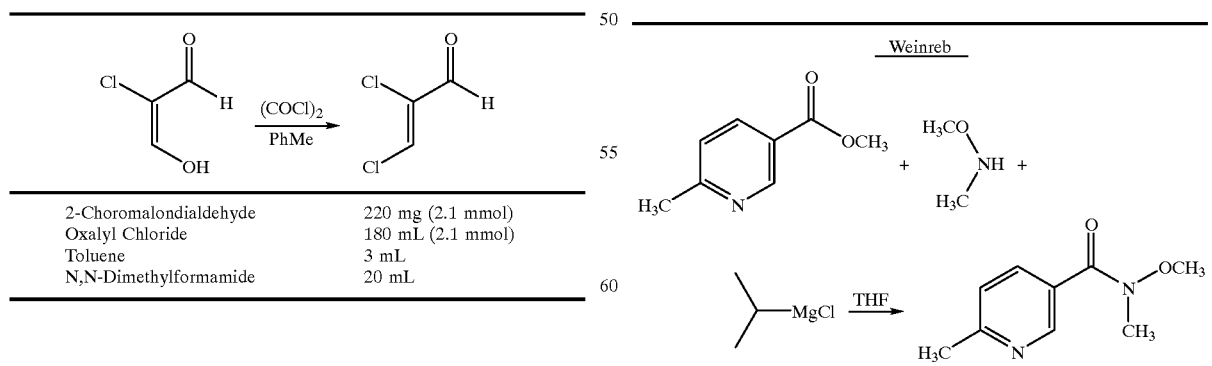

| | |
|---|---|
| 2-Choromalondialdehyde | 220 mg (2.1 mmol) |
| Oxalyl Chloride | 180 mL (2.1 mmol) |
| Toluene | 3 mL |
| N,N-Dimethylformamide | 20 mL |

N,N-dimethyl formamide was added to a slurry of 2-chloromalondialdehyde (220 mg) in toluene. Oxalyl chloride was added and the reaction mixture was stirred until complete dissolution occurred.

| | |
|---|---|
| Ketone B | 500 mg (1.8 mmol) |
| Lithium bis(trimethylsilyl)amide (1M in THF) | 1.8 mL (1.8 mmol) |
| Tetrahydrofuran | 15 mL |
| 2,3-Dichloroacrolein in toluene | 2.1 mmol in 3 mL toluene |
| Ammonium acetate | 1.0 g |

Lithium bis(trimethylsilyl)amide (1.8 mL;1 M in THF) was added dropwise to ketone B (500 mg) in THF (15 mL) at −78° C. The reaction mixture was warmed to ambient temperature for 1 hour to form the lithium enolate of B (see the generic formula B1) before recooling to −78° C. A solution of 2,3-dichloroacrolein was added and the temperature allowed to warm to room temperature. After 1 hour ammonia gas was passed through the solution and after 30 minutes ammonium acetate (1 g) was added. The reaction mixture was warmed to 60° C. for 1 hour and poured into aqueous sodium hydroxide (2 M; 100 mL). The product was extracted with dichloromethane (2×150 mL), dried (MgSO4) and the solvent removed to afford 1 (500 mg; 80%).

EXAMPLE 2

| | |
|---|---|
| Methyl 6-methylnicotinate | 21.56 g (0.143 mol) |
| N,O-Dimethylhydroxyamine | 13.9 g (0.229 mol) |
| Tetrahydrofuran | 150 mL |

-continued

Weinreb

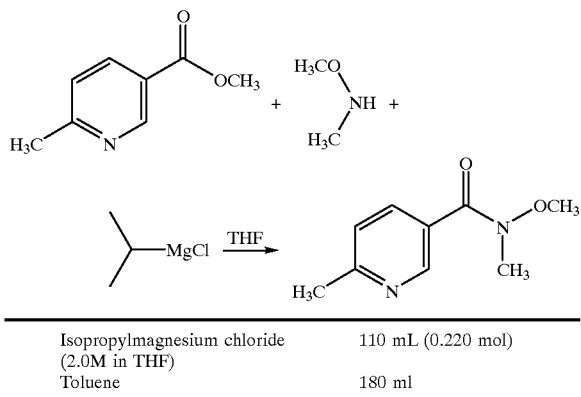

| Isopropylmagnesium chloride (2.0M in THF) | 110 mL (0.220 mol) |
| --- | --- |
| Toluene | 180 ml |

A solution of Methyl 6-methylnicotinate (21.56 g), and N,O-dimethylhydroxylamine (13.9 g) in THF (150 mL) was cooled to −10° C. Isopropylmagnesium chloride (110 mL) was added over 2.5 h. The reaction mixture was poured into aqueous acetic acid (10 vol %, 126 mL) at 5 ° C. Toluene (60 mL) was added to the mixture, then the layers were separated. The aqueous layer was extracted with toluene (2×60 mL) and the solvent removed. Solid impurities were removed by filtration and the filtrate was concentrated to afford the Weinreb amide as a light orange oil (24.2 g, 94.3%).

EXAMPLE 3

Grinard

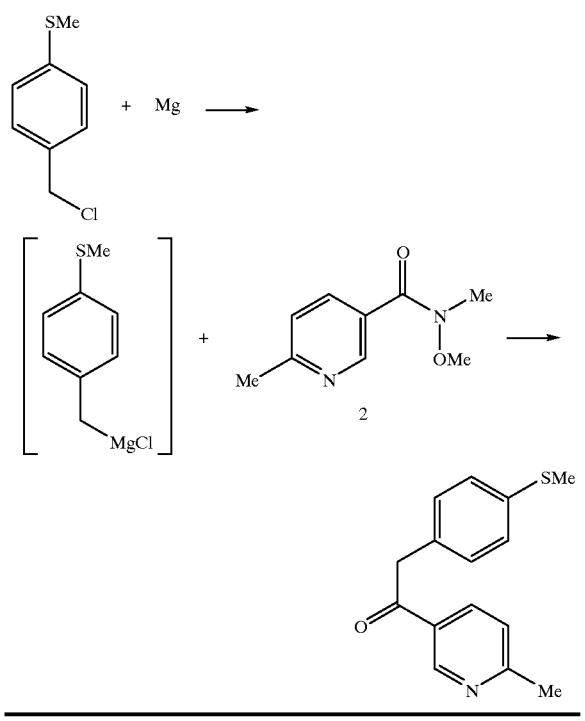

| 4-thiomethylbenzyl chloride | 566 g (3.28 mol) |
| --- | --- |
| Magnesium | 191 g (7.86 mol) |

-continued

Grinard

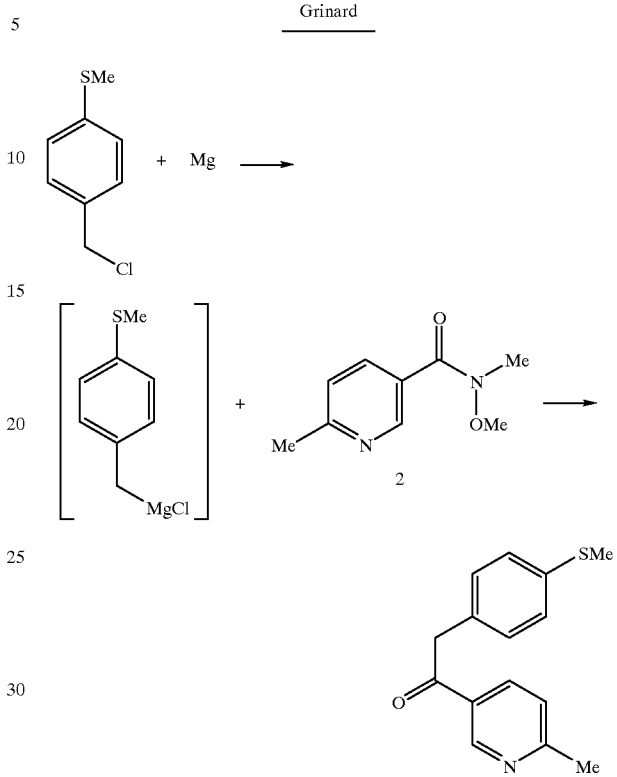

| Toluene | 9 L |
| --- | --- |
| Tetrahydrofuran | 0.545 L |
| Weinreb amide 2 | 300 g (1.66 mol) |

A mixture of magnesium (191 g, 7.86 mol) toluene (4L), 4-thiomethylbenzyl chloride (566 g, 3.28 mol) and tetrahydrofuran (0.545L, 6.73 mol) were charged over 3–4 hours. An additional flask was charged with Weinreb amide (300 g, 1.66 mol) and toluene (1.7L) and cooled to −20 ° C. The Grignard solution prepared above was added over 30 minutes and the mixture was aged for 1 hour. The reaction mixture as quenched by the addition of 50% aqueous acetic acid (0.5L). Toluene (1L) and water (1L) were added and the layers were separated. The aqueous layer wasextracted with toluene (2×2L). The combined organic extracts were extracted with dilute hydrochloric acid (1×2L). Ethyl acetate was added to the aqueous layer and the pH was adjusted with ammonia (0.6L). The phases were separated and the aqueous layer was extracted with ethyl acetate (2×1.25L). The combined extracts were concentrated on a rotary evaporator to give a light yellow solid (326.5 g, 76%)

EXAMPLE 4

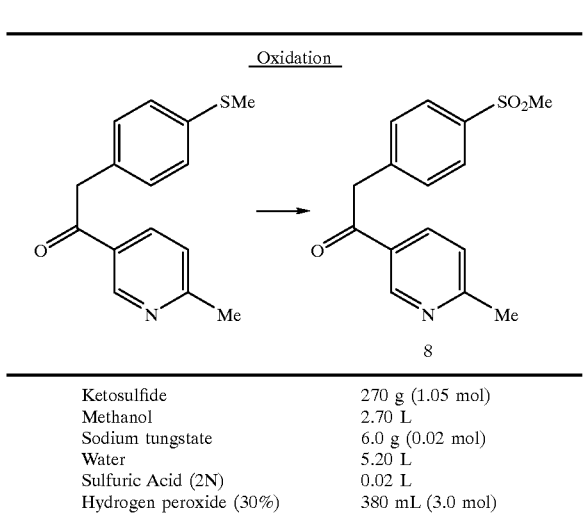

| Ketosulfide | 270 g (1.05 mol) |
|---|---|
| Methanol | 2.70 L |
| Sodium tungstate | 6.0 g (0.02 mol) |
| Water | 5.20 L |
| Sulfuric Acid (2N) | 0.02 L |
| Hydrogen peroxide (30%) | 380 mL (3.0 mol) |

A mixture of ketosulfide (270 g, 1.05 mol), sulfuric acid (2N) (20 mL), and methanol (2.70L) was heated at 55° C. An aqueous solution of sodium tungstate (6.0 g, 0.02 mol) was added then hydrogen peroxide (380 mL) was added over 1 hour. Water (3L) was added and the mixture was cooled to ambient temperature then filtered. The solids were washed with water (2L) and dried under vacuum with a stream of nitrogen to give ketosulfone 8 (250.2 g, 82.5%) as a colorless solid.

EXAMPLE 5

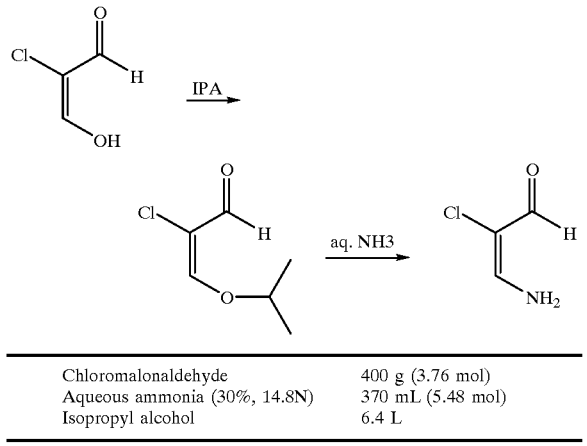

| Chloromalonaldehyde | 400 g (3.76 mol) |
|---|---|
| Aqueous ammonia (30%, 14.8N) | 370 mL (5.48 mol) |
| Isopropyl alcohol | 6.4 L |

To a flask was charged with chloromalonaldehyde (400 g, 3.76 mol), and isopropyl alcohol (400 mL). The solution was concentrated under reduced pressure with a continuous, slow feed of isopropyl alcohol (4.0 L total). The resulting dark brown liquid was diluted with isopropyl alcohol (400 mL). The mixture was added to a cooled (5° C.) solution of 30% aqueous ammonia (370 mL) in isopropyl alcohol (2 L). The mixture was aged for 3 hours and the product was collected by filtration (373 g, 93%)

EXAMPLE 5A

A number of routes are available for the preparation of chloromalondialdehyde.

Preparation from 1,1,2,3,3-Pentachloropropane

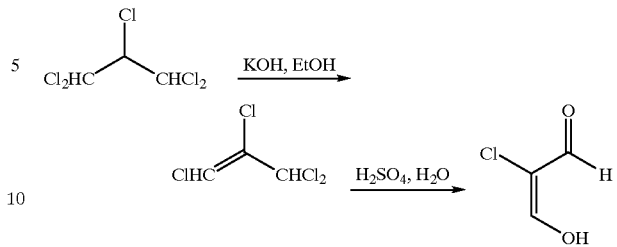

A detailed experimental is published in Houben-Weyl-Muller: Methoden der Organischen Chemie, 4th Edit., Vol 7/1, Thieme Verlag, Stuttgart, 1954, page 119. The starting material 1,1,2,3,3-pentachloropropane is commercially available from Pfaltz and Bauer.

Preparation from Mucochloric Acid

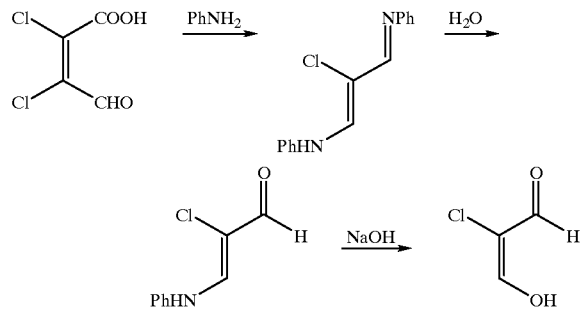

The following is a slight variation of the original procedure of Dieckmann (*Ber. Deut. Chem. Ges.* 1904, 37, 4638).

| Mucochloric acid | 50.0 g (0.30 mol) |
|---|---|
| Aniline | 54 mL (0.60 mol) |
| Water | 1000 mL |

To a solution of aniline in water at 85° C. in a vigorously stirred 2 L flask was added mucochloric acid in small portions over 30 min. On addition of the mucochloric acid, a yellow color develops, which quickly dissipated. The reaction mixture stayed heterogeneous and filtration of an aliquot after 30 min heating indicated completion of the reaction.

The reaction mixture was heated at 90° C. for 60 min., cooled to 50° C. and filtered. The filtercake was washed with 50 mL of 2N HCl and 100 mL of $H_2O$. The product was dried in a $N_2$ stream to give 57 g (100% yield) of 3-anilido-2-chloro-acrolein as a gray solid. $^{13}C$ NMR ($D_6$-DMSO in ppm):108, 117, 124, 129, 140. 147, 182.

A solution of 3-anilido-2-chloro-acrolein in 120 mL of 5N NaOH was heated to 100° C. for 90 min. The dark black solution was extracted twice with 50 mL each of MTBE.

The first organic wash removed most of the dark color from the solution, and the second organic wash was only lightly colored.

On cooling the aqueous phase, a crystalline precipitate formed. This product was the 3-chloromalondialdehyde Na salt.

The aqueous phase was acidified by the addition of 60 mL of 37% HCl solution. The aqueous phase was extracted (MTBE/THF 50/50, 400 mL total) and the combined organic phases were dried over MgSO4. After treatment with Darco G60 and filtration through a plug of SiO2, the solution was evaporated to give 19.6 g (62% overall yield) of chloromalondialdehyde as a dark solid. Recrystallization from ca. 10 mL of MTBE gave 11.13 g of pure chloromalondialdehyde as a tan solid. $^{13}$C NMR (D6-DMSO in ppm): 113, 175 (broad).

Preparation from Chloroacetylchloride

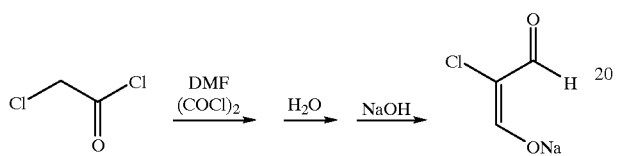

Arnold (*Collect. Czech. Chem. Commun.* 1961, 26, 3051) mentions the formation of 3-dimethylamino-2-chloro-acrolein by reaction of chloroacetic acid with the Vilsmeyer reagent derived from POCl$_3$ and DMF. A variation and extension of his procedure prepares chloromalondialdehyde as its Na salt.

Oxalylchloride (280 mL, 3.2 mol) was added at 10° C. to 1000 mL of DMF. The reaction was highly exothermic and a heavy precipitate formed. After a 2 h age, chloroacetylchloride (110 mL, 1.4 mol) was added and the reaction mixture was warmed to 75° C. for 3 hours. Analysis of an aliquot by $^1$H NMR indicated complete consumption of the chloroacetylchloride and the reaction mixture was quenched by addition into 1 L of H$_2$O. To the cooled solution was added 500 mL of a 50% NaOH solution. The reaction mixture is heated to reflux for 5 hours. On cooling a precipitate formed, which was filtered and washed with water. The tan solid was dried in a N$_2$ stream to give 84 g of a tan solid (54% yield).

What is claimed is:

1. A process for making a compound of formula 13

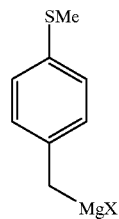

13 wherein X is a halogen belonging to the group consisting of iodide, chloride, bromide and fluoride;

comprising reacting a compound of formula 12

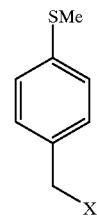

12 with magnesium in the presence of a solvent/co-solvent mixture to yield a compound of formula 13.

2. A process according to claim 1 wherein X is chloride.

3. A process according to claim 1 wherein the solvent/co-solvent mixture is selected from the group consisting of toluene/tetrahydrofuran, tetrahydrofuran/diethylether, toluene/diethylether, tetrahydrofuran/methyl-t-butylether, toluene/methyl-t-butylether, toluene/dioxane and tetrahydrofuran/dioxane.

4. A process according to claim 3 wherein the solvent/co-solvent mixture is toluene/tetrahydrofuran.

5. A process according to claim 1 wherein the molar ratio of solvent to co-solvent is from about 0.5:4 to about 1:1.

6. A process according to claim 5 wherein the molar ratio of solvent to co-solvent is from about 1:2 to about 1:1.

* * * * *